US007292139B2

(12) United States Patent (10) Patent No.: US 7,292,139 B2
Mazar et al. (45) Date of Patent: *Nov. 6, 2007

(54) REPEATER DEVICE FOR COMMUNICATIONS WITH AN IMPLANTABLE MEDICAL DEVICE

(75) Inventors: Scott T. Mazar, Inver Grove Heights, MN (US); Yatheendhar D. Manicka, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 121 days.

This patent is subject to a terminal disclaimer.

(21) Appl. No.: 11/327,879

(22) Filed: Jan. 9, 2006

(65) Prior Publication Data

US 2006/0121846 A1 Jun. 8, 2006

Related U.S. Application Data

(63) Continuation of application No. 10/321,885, filed on Dec. 17, 2002, now Pat. No. 7,009,511.

(51) Int. Cl.
*G08B 1/00* (2006.01)
(52) U.S. Cl. .............. 340/531; 340/539.1; 340/539.11; 340/539.12; 705/2; 705/3
(58) Field of Classification Search ................ 340/531, 340/539.1, 539.11, 539.12, 573.1, 573.4, 340/286.07, 825.19; 705/2, 3
See application file for complete search history.

(56) References Cited

U.S. PATENT DOCUMENTS 4,142,533 A 3/1979 Brownlee et al.

4,531,527 A 7/1985 Reinhold, Jr. et al.

(Continued)

FOREIGN PATENT DOCUMENTS

EP 0 342 859 11/1989

(Continued)

OTHER PUBLICATIONS

Moody GB, "Integration of Real-Time and Off-Line Clinical Data in the MIMIC Database," Computers in Cardiology 1997 vol. 24, pp. 585-588, Cambridge, MA USA.

(Continued)

*Primary Examiner*—Daryl C Pope
(74) *Attorney, Agent, or Firm*—Patrick J. S. Inouye; Krista A. Wittman

(57) ABSTRACT

A repeater device for an advanced patient management system communicates with a medical device coupled to a patient to obtain data about the medical device and/or patient's condition. The repeater device maintains the data while if considers various factors when coordinating transfer of the data to a repository of the advanced patient management system. The repeater device may be configured to analyze the data to determine a degree of urgency, such as whether an emergency exists, and then determine when to transfer the data based on the degree of urgency. The repeater device may also be configured to test the condition of the communication medium being used to transfer the data to the repository, such as determining whether a telephone line is in use, and then determine when to transfer the data based on the condition of the of the communication medium.

41 Claims, 7 Drawing Sheets

U.S. PATENT DOCUMENTS

| | | |
|---|---|---|
| 4,658,831 A | 4/1987 | Reinhard et al. |
| 4,681,111 A | 7/1987 | Silvian |
| 4,686,999 A | 8/1987 | Snyder et al. |
| 4,705,043 A | 11/1987 | Imran |
| 4,757,816 A | 7/1988 | Ryan et al. |
| 4,793,353 A | 12/1988 | Borkan |
| 4,809,697 A | 3/1989 | Causey et al. |
| 4,852,570 A | 8/1989 | Levine |
| 4,932,408 A | 6/1990 | Schaldach |
| 4,947,407 A | 8/1990 | Silvian |
| 4,952,928 A * | 8/1990 | Carroll et al. ........... 340/10.41 |
| 4,958,645 A | 9/1990 | Cadell et al. |
| 4,969,464 A | 11/1990 | Callaghan et al. |
| 4,974,607 A | 12/1990 | Miwa |
| 4,987,897 A | 1/1991 | Funke |
| 5,040,536 A | 8/1991 | Riff |
| 5,058,581 A | 10/1991 | Silvian |
| 5,081,987 A | 1/1992 | Nigam |
| 5,113,859 A | 5/1992 | Funke |
| 5,113,869 A | 5/1992 | Nappholz et al. |
| 5,117,825 A | 6/1992 | Grevious |
| 5,133,346 A | 7/1992 | Kulkarni |
| 5,137,022 A | 8/1992 | Henry |
| 5,199,428 A | 4/1993 | Obel et al. |
| 5,241,961 A | 9/1993 | Henry |
| 5,292,343 A | 3/1994 | Blanchette et al. |
| 5,331,549 A | 7/1994 | Crawford, Jr. |
| 5,331,966 A | 7/1994 | Bennett et al. |
| 5,336,245 A | 8/1994 | Adams et al. |
| 5,350,411 A | 9/1994 | Ryan et al. |
| 5,355,889 A | 10/1994 | Nevo et al. |
| 5,357,427 A | 10/1994 | Langen et al. |
| 5,383,915 A | 1/1995 | Adams |
| 5,390,238 A | 2/1995 | Kirk et al. |
| 5,413,594 A | 5/1995 | Williams |
| 5,415,181 A | 5/1995 | Hogrefe et al. |
| 5,416,695 A | 5/1995 | Stutman et al. |
| 5,421,343 A | 6/1995 | Feng |
| 5,437,278 A | 8/1995 | Wilk |
| 5,438,983 A | 8/1995 | Falcone |
| 5,458,122 A | 10/1995 | Hethuin |
| 5,464,012 A | 11/1995 | Falcone |
| 5,476,485 A | 12/1995 | Weinberg et al. |
| 5,481,262 A | 1/1996 | Urbas et al. |
| 5,509,927 A | 4/1996 | Epstein et al. |
| 5,522,865 A | 6/1996 | Schulman et al. |
| 5,544,661 A | 8/1996 | Davis et al. |
| 5,549,654 A | 8/1996 | Powell |
| 5,553,609 A | 9/1996 | Chen et al. |
| 5,576,952 A | 11/1996 | Stutman |
| 5,584,868 A | 12/1996 | Salo et al. |
| 5,591,215 A | 1/1997 | Greenhut et al. |
| 5,603,331 A | 2/1997 | Heemels et al. |
| 5,626,630 A | 5/1997 | Markowitz et al. |
| 5,629,678 A | 5/1997 | Gargano et al. |
| 5,630,836 A | 5/1997 | Prem et al. |
| 5,660,183 A | 8/1997 | Chiang et al. |
| 5,674,249 A | 10/1997 | De Coriolis et al. |
| 5,683,432 A | 11/1997 | Goedeke et al. |
| 5,687,734 A | 11/1997 | Dempsey et al. |
| 5,697,959 A | 12/1997 | Poore |
| 5,704,366 A | 1/1998 | Tracklind et al. |
| 5,711,297 A | 1/1998 | Iliff |
| 5,713,350 A | 2/1998 | Yokota et al. |
| 5,713,937 A | 2/1998 | Nappholz et al. |
| 5,720,770 A | 2/1998 | Nappholz et al. |
| 5,720,771 A | 2/1998 | Snell |
| 5,724,580 A | 3/1998 | Levi et al. |
| 5,724,983 A | 3/1998 | Selker et al. |
| 5,738,102 A | 4/1998 | Lemelson |
| 5,741,315 A | 4/1998 | Lee et al. |
| 5,743,267 A | 4/1998 | Nikolic et al. |
| 5,749,907 A | 5/1998 | Mann |
| 5,749,908 A | 5/1998 | Snell |
| 5,752,976 A | 5/1998 | Duffin et al. |
| 5,752,977 A | 5/1998 | Grevious et al. |
| 5,766,232 A | 6/1998 | Grevious et al. |
| 5,769,074 A | 6/1998 | Barnhill et al. |
| 5,769,876 A | 6/1998 | Silvian |
| 5,772,586 A | 6/1998 | Heinonen et al. |
| 5,772,604 A | 6/1998 | Langberg et al. |
| 5,774,501 A | 6/1998 | Halpern et al. |
| 5,778,882 A | 7/1998 | Raymond et al. |
| 5,785,650 A | 7/1998 | Akasaka et al. |
| 5,791,342 A | 8/1998 | Woodard |
| 5,792,062 A | 8/1998 | Poon et al. |
| 5,792,207 A | 8/1998 | Dietrich |
| 5,814,089 A | 9/1998 | Stokes et al. |
| 5,819,251 A | 10/1998 | Kremer et al. |
| 5,836,983 A | 11/1998 | Weijand et al. |
| 5,843,133 A | 12/1998 | Routh et al. |
| 5,843,139 A | 12/1998 | Goedeke et al. |
| 5,855,593 A | 1/1999 | Olson et al. |
| 5,860,918 A | 1/1999 | Schradi et al. |
| 5,861,014 A | 1/1999 | Familoni |
| 5,861,018 A | 1/1999 | Feierbach |
| 5,876,353 A | 3/1999 | Riff |
| 5,879,375 A | 3/1999 | Larson, Jr. et al. |
| 5,891,178 A | 4/1999 | Mann et al. |
| 5,897,493 A | 4/1999 | Brown |
| 5,899,928 A | 5/1999 | Sholder et al. |
| 5,899,931 A | 5/1999 | Deschamp et al. |
| 5,911,132 A | 6/1999 | Sloane |
| 5,917,414 A | 6/1999 | Oppelt et al. |
| 5,919,214 A | 7/1999 | Ciciarelli et al. |
| 5,931,857 A | 8/1999 | Prieve |
| 5,935,078 A | 8/1999 | Feierbach |
| 5,944,659 A | 8/1999 | Flach et al. |
| 5,954,640 A | 9/1999 | Szabo |
| 5,957,861 A | 9/1999 | Combs et al. |
| 5,974,124 A | 10/1999 | Schlueter, Jr. et al. |
| 5,987,352 A | 11/1999 | Klein et al. |
| 5,999,857 A | 12/1999 | Weijand et al. |
| 6,024,699 A | 2/2000 | Surwit et al. |
| 6,047,203 A | 4/2000 | Sackner et al. |
| 6,050,940 A | 4/2000 | Braun |
| 6,067,466 A | 5/2000 | Selker |
| 6,073,046 A | 6/2000 | Patel |
| 6,080,106 A | 6/2000 | Lloyd et al. |
| 6,083,248 A | 7/2000 | Thompson |
| 6,093,146 A | 7/2000 | Filangeri |
| 6,095,985 A | 8/2000 | Raymond et al. |
| 6,102,856 A | 8/2000 | Groff et al. |
| 6,122,351 A | 9/2000 | Schlueter, Jr. et al. |
| 6,139,494 A | 10/2000 | Cairnes |
| 6,141,584 A | 10/2000 | Rockwell et al. |
| 6,155,267 A | 12/2000 | Nelson |
| 6,168,563 B1 | 1/2001 | Brown |
| 6,170,488 B1 | 1/2001 | Spillman, Jr. et al. |
| 6,171,237 B1 | 1/2001 | Avitall et al. |
| 6,171,256 B1 | 1/2001 | Joo et al. |
| 6,185,452 B1 | 2/2001 | Schulman et al. |
| 6,200,264 B1 | 3/2001 | Satherley et al. |
| 6,206,835 B1 | 3/2001 | Spillman, Jr. et al. |
| 6,208,894 B1 | 3/2001 | Schulman et al. |
| 6,213,942 B1 | 4/2001 | Flach et al. |
| 6,216,038 B1 | 4/2001 | Hartlaub et al. |
| 6,223,078 B1 | 4/2001 | Marcovecchio |
| 6,223,083 B1 | 4/2001 | Rosar |
| 6,225,901 B1 | 5/2001 | Kail, IV |
| 6,236,889 B1 | 5/2001 | Soykan et al. |
| 6,246,992 B1 | 6/2001 | Brown |
| 6,249,705 B1 | 6/2001 | Snell |
| 6,250,309 B1 | 6/2001 | Krichen et al. |

| | | |
|---|---|---|
| 6,263,245 B1 | 7/2001 | Snell |
| 6,263,246 B1 | 7/2001 | Goedeke et al. |
| 6,263,247 B1 | 7/2001 | Mueller et al. |
| 6,287,252 B1 | 9/2001 | Lugo |
| 6,289,238 B1 | 9/2001 | Besson et al. |
| 6,290,646 B1 | 9/2001 | Cosentino et al. |
| 6,292,698 B1 | 9/2001 | Duffin et al. |
| 6,302,844 B1 | 10/2001 | Walker |
| 6,304,788 B1 | 10/2001 | Eady et al. |
| 6,319,200 B1 | 11/2001 | Lai et al. |
| 6,329,929 B1 | 12/2001 | Weijand et al. |
| 6,336,900 B1 | 1/2002 | Alleckson |
| 6,345,203 B1 | 2/2002 | Mueller et al. |
| 6,349,234 B2 | 2/2002 | Pauly et al. |
| 6,363,282 B1 | 3/2002 | Nichols et al. |
| 6,416,471 B1 | 7/2002 | Kumar et al. |
| 6,418,346 B1 | 7/2002 | Nelson et al. |
| 6,442,432 B2 | 8/2002 | Lee |
| 6,442,433 B1 | 8/2002 | Linberg |
| 6,454,705 B1 | 9/2002 | Cosentino |
| 6,477,242 B1 | 11/2002 | Freeny, Jr. |
| 6,477,424 B1 | 11/2002 | Thompson et al. |
| 6,480,745 B2 | 11/2002 | Nelson et al. |
| 6,485,418 B2 | 11/2002 | Yasushi et al. |
| 6,497,657 B2 | 12/2002 | Nunome |
| 6,544,171 B2 | 4/2003 | Beetz et al. |
| 6,544,173 B2 | 4/2003 | West et al. |
| 6,544,174 B2 | 4/2003 | West et al. |
| 6,564,104 B2 | 5/2003 | Nelson et al. |
| 6,569,094 B2 | 5/2003 | Suzuki et al. |
| 6,577,901 B2 | 6/2003 | Thompson |
| 6,599,250 B2 | 7/2003 | Webb et al. |
| 6,602,191 B2 | 8/2003 | Quy |
| 6,622,050 B2 | 9/2003 | Thompson |
| 6,687,547 B2 | 2/2004 | Goedeke et al. |
| 6,754,538 B2 | 6/2004 | Linberg |
| 6,780,156 B2 | 8/2004 | Haueter et al. |
| 6,804,558 B2 | 10/2004 | Haller et al. |
| 6,824,512 B2 | 11/2004 | Warkentin et al. |
| 6,827,670 B1 | 12/2004 | Stark et al. |
| 6,893,396 B2 | 5/2005 | Schulze et al. |
| 7,009,511 B2 * | 3/2006 | Mazar et al. ............... 340/531 |
| 2001/0044588 A1 | 11/2001 | Mault |
| 2001/0051787 A1 | 12/2001 | Haller et al. |
| 2002/0013538 A1 | 1/2002 | Teller |
| 2002/0013613 A1 | 1/2002 | Haller et al. |
| 2002/0019586 A1 | 2/2002 | Teller et al. |
| 2002/0052539 A1 | 5/2002 | Haller et al. |
| 2002/0072785 A1 | 6/2002 | Nelson et al. |
| 2002/0095196 A1 | 7/2002 | Linberg |

FOREIGN PATENT DOCUMENTS

| | | |
|---|---|---|
| EP | 0 513 457 | 11/1992 |
| EP | 0 531 889 A2 | 3/1993 |
| EP | 0 554 955 | 8/1993 |
| EP | 0 711 531 A1 | 5/1996 |
| WO | WO 97/39792 | 10/1997 |
| WO | WO 98/07142 | 2/1998 |
| WO | WO 99/46718 | 9/1999 |

OTHER PUBLICATIONS

Long WJ, et al., "Differential Diagnosis Generation From A Causal Network With Probabilities," Computers in Cardiology, 1988, Proceedings, pp. 185-188, Washington DC, USA.

* cited by examiner

REPEATER DEVICE FOR COMMUNICATIONS WITH AN IMPLANTABLE MEDICAL DEVICE

CROSS-REFERENCE TO RELATED APPLICATION

This patent application is a continuation of U.S. patent application Ser. No. 10/321,885, filed Dec. 17, 2002, now U.S. Pat. No. 7,009,511 issued Mar. 7, 2006, the priority of filing date of which is claimed, and the disclosure of which is incorporated by reference.

FIELD OF THE INVENTION

The present relay device relates generally to advanced patient management systems, and more specifically to providing information between a medical device and a repository of the advanced patient management system through a repeater device.

BACKGROUND OF THE INVENTION

In an effort to limit the number of follow-ups necessary to monitor the device and the data that it acquires, an advanced patient management system may provide a communication infrastructure. This infrastructure allows the implantable medical device to communicate over long distances at virtually any time with a backend system that monitors the implantable device and the patient. Furthermore, this backend system allows monitoring of the patient on a more frequent basis than ordinary follow-up visits can practically allow. The back end system communicates with the implantable device through a repeater that the patient keeps in close proximity. The conventional repeater device interrogates the medical device through some form of wireless communication such as inductive coupling. The repeater device retrieves data from the medical device and transmits the data through another communication medium, such as a standard telephone line, to the remote location.

Some conventional repeater devices form a direct line of communication between the medical device and the remote location and thereby act as a conduit for the data. Generally, the patient operates these conventional repeater devices and must initiate the communication of the data at appropriate times. Other conventional repeater devices may retrieve the data from the medical device at an appropriate time and maintain it until another appropriate time when it is sent to the remote location. However, the patient must also initiate the communication between these conventional repeater devices and the remote location, or the repeater device uses a preset timer to initiate communication without regard for additional considerations.

Requiring the patient to initiate communication with the remote location is overly burdensome, especially in situations where the repeater device collects data at one time and then at some later time sends the data to the remote location. Furthermore, requiring the patient to initiate communications with the remote location makes the advanced patient management system vulnerable to human error. Relying solely on a preset timer to initiate communications with the remote location is also problematic. For example, the telephone line relied upon by the repeater device may be in use or is otherwise unavailable at the preset time, or an emergency situation may be occurring that requires immediate attention rather than communication after a preset delay period.

SUMMARY OF THE INVENTION

The problems discussed above and others are addressed by various embodiments of the present invention. These embodiments allow the repeater device to automatically communicate with the remote location to transfer the patient data. The repeater device automatically communicates with the remote location by initiating communication after considering additional factors such as the accessibility or condition of the communications medium being used to pass the data and/or whether the condition of the patient requires immediate attention.

In one embodiment, the repeater device coordinates the transfer of data from the medical device to a data repository based upon the condition of a communications medium existing between the repeater device and the repository. The repeater device stores the data in memory after it has been retrieved from the implantable device and then begins detecting the condition of the communication medium, such as whether the telephone line is already in use or is available for placing a call. Once the communication medium has an adequate condition for transferring the data, the repeater device sends the data over the communication medium to the repository.

In another embodiment, the repeater device coordinates the transfer of data from the medical device to the data repository based upon the urgency of the data that has been retrieved from the medical device. The repeater device stores the data in memory after it has been retrieved from the implantable device and then begins to analyze the data to determine its degree of urgency, such as to determine whether the patient is about to or is already experiencing an emergency condition. The repeater then determines the time to send the data to the repository based on the degree of urgency.

These and various other features as well as advantages, which characterize the present invention, will be apparent from a reading of the following detailed description and a review of the associated drawings.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Prior to discussing the devices and communication protocols of the embodiments of the present invention, an example of an advanced patient management system is discussed to provide an example of an environmental context for the embodiments of the present invention. However, it is to be understood that the advanced patient management system described herein in conjunction with the embodiments of the present invention is only one example of an environmental context and that the embodiments of the present invention are applicable to other environmental contexts that may or may not include an advanced patient management system. The devices and communication protocols of the embodiments of the present invention are described below with reference to FIGS. 5-10 and section V. Repeater Communications.

An advanced patient management system is configured to collect patient-specific information, store and collate the information, and generate actionable recommendations to enable the predictive management of patients. The advanced patient management system is also configured to leverage a remote communications infrastructure to provide automatic device follow-ups to collect data, coordinate therapy, and to determine if remote devices are functioning properly. The term "patient" is used herein to mean any individual from whom information is collected. The term "caregiver" is used herein to mean any provider of services, such as health care providers including, but not limited to, nurses, doctors, and other health care provider staff.

Figure 1:
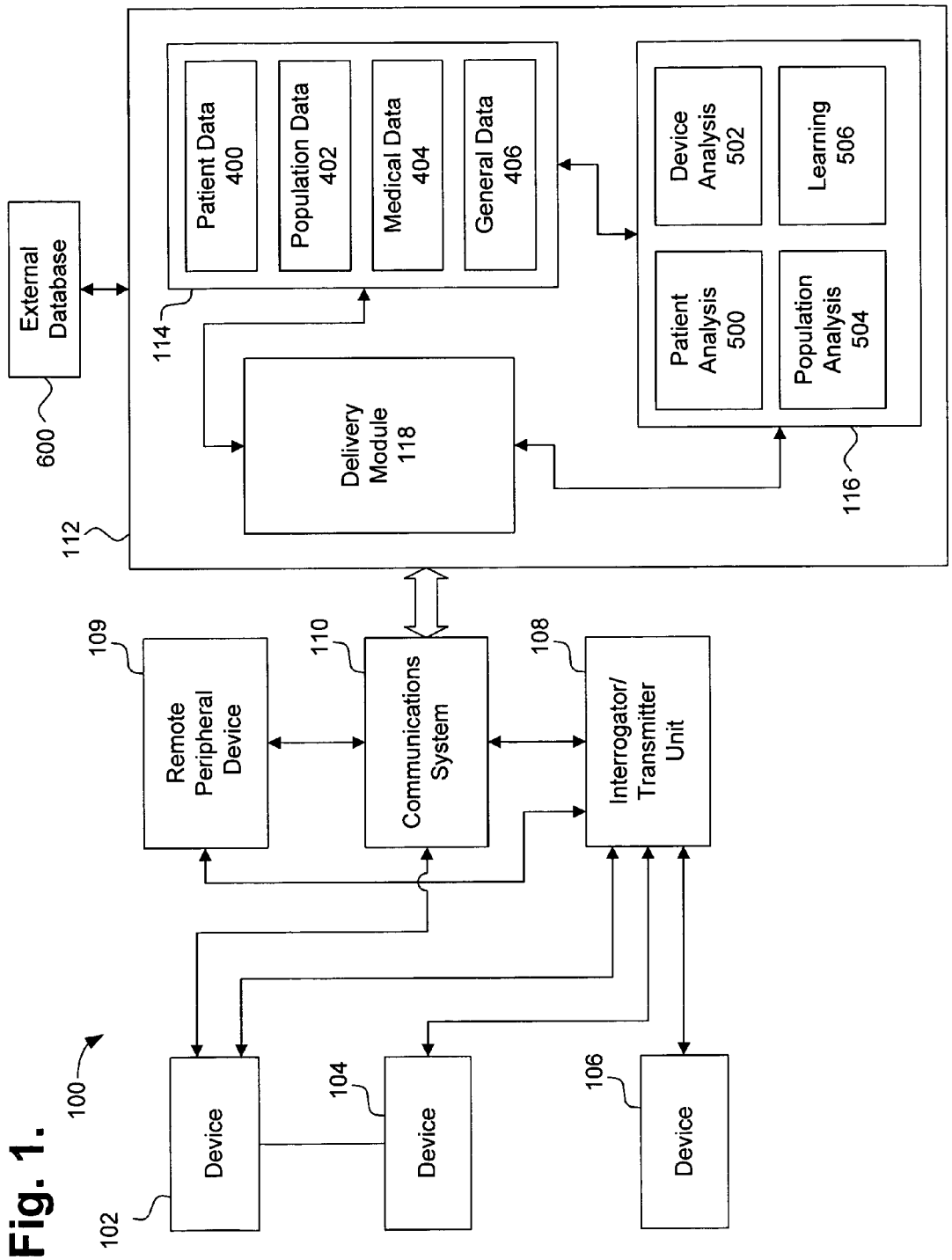
FIG. 1 illustrates an example advanced patient management system.

FIG. 1 illustrates an example advanced patient management system 100. Advanced patient management system 100 generally includes the following components: one or more devices 102, 104, and 106, one or more interrogator/transceiver units 108, a communication system 110, one or more remote peripheral devices 109, and a host 112.

Each component of the advanced patient management system 100 can communicate using the communication system 110. Some components may also communicate directly with one another. For example, devices 102 and 104 may be configured to communicate directly with one another. The various components of the example advanced patient management system 100 illustrated herein are described below.

Devices

Devices 102, 104, and 106 can be implantable devices or external devices that may provide one or more of the following functions with respect to a patient: (1) sensing, (2) data analysis, and (3) therapy. For example, in one embodiment, devices 102, 104, and 106 are either implanted or external devices used to measure a variety of physiological, subjective, and environmental conditions of a patient using electrical, mechanical, and/or chemical means. The devices 102, 104, and 106 can be configured to automatically gather data or can require manual intervention by the patient. The devices 102, 104, and 106 can be configured to store data related to the physiological and/or subjective measurements and/or transmit the data to the communication system 110 using a variety of methods, described in detail below. Although three devices 102, 104, and 106 are illustrated in the example embodiment shown, more or fewer devices may be used for a given patient.

The devices 102, 104, and 106 can be configured to analyze the measured data and act upon the analyzed data. For example, the devices 102, 104, and 106 are configured to modify therapy or provide alarm indications based on the analysis of the data.

In one embodiment, devices 102, 104, and 106 also provide therapy. Therapy can be provided automatically or in response to an external communication. Devices 102, 104, and 106 are programmable in that the characteristics of their sensing, therapy (e.g., duration and interval), or communication can be altered by communication between the devices 102, 104, and 106 and other components of the advanced patient management system 100. Devices 102, 104, and 106 can also perform self-checks or be interrogated by the communication system 110 to verify that the devices are functioning properly. Examples of different embodiments of the devices 102, 104, and 106 are provided below.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance.

A heart rhythm sensor, typically found in a pacemaker or defibrillator, is one example of an implantable device. In the heart, an electrical wave activates the heart muscle just prior to contraction. As is known in the art, electrical circuits and lead-wires transduce the heart's activation event and reject other, non-essential electrical events. By measuring the time interval between activation events, the heart rhythm can be determined. A transthoracic impedance sensor is another example of a sensor in an implantable device. During the respiratory cycle, large volumes of air pass into and out of the body. The electrical resistance of the thorax changes markedly as a result of large differences in conductivity of air and body tissues. The thoracic resistance can be measured during respiration and converted into a measurable electrical signal (i.e., impedance) so that breathing rate and profile can be approximated. Implantable devices can also sense chemical conditions, such as glucose levels, blood oxygen levels, etc. Further, the advanced patient management system 100 may utilize other implantable devices as well that provide physiological measurements of the patient, such as drug pumps, neurological devices (e.g., stimulators), oxygen sensors, etc.

Derived measurements can also be determined from the implantable device sensors. For example, a sleep sensor can rely on measurements taken by an implanted accelerometer that measures body activity levels. The sleep sensor can estimate sleeping patterns based on the measured activity levels. Other derived measurements include, but are not limited to, a functional capacity indicator, autonomic tone indicator, sleep quality indicator, cough indicator, anxiety indicator, and cardiovascular wellness indicator for calculating a quality of life indicator quantifying a patient's overall health and well-being.

Devices 102, 104, and 106 can also be external devices, or devices that are not implanted in the human body, that are used to measure physiological data. Such devices include a multitude of devices to measure data relating to the human body, such as temperature (e.g., a thermometer), blood pressure (e.g., a sphygmomanometer), blood characteristics (e.g., glucose levels), body weight, physical strength, mental acuity, diet, heart characteristics, and relative geographic position (e.g., a Global Positioning System (GPS)).

Devices 102, 104, and 106 can also be environmental sensors. The devices can be placed in a variety of geographic locations (in close proximity to patient or distributed throughout a population) and record non-patient specific characteristics such as, but not limited to, temperature, air quality, humidity, carbon monoxide level, oxygen level, barometric pressure, light intensity, and sound.

One or more of the devices 102, 104, and 106 (for example, device 106) may be external devices that measure subjective or perceptive data from the patient. Subjective data is information related to a patient's feelings, perceptions, and/or opinions, as opposed to objective physiological data. For example, the "subjective" devices can measure patient responses to inquiries such as "How do you feel?" and "How is your pain?" The device can prompt the patient and record subjective data from the patient using visual and/or audible cues. For example, the patient can press coded response buttons or type an appropriate response on a keypad. Alternatively, subjective data may be collected by allowing the patient to speak into a microphone and using speech recognition software to process the subjective data.

In one example embodiment, the subjective device presents the patient with a relatively small number of responses to each question posed to the patient. For example, the responses available to the patient may include three faces representing feelings of happiness, nominalness, and sadness. Averaged over time, a trend of a patient's well being will emerge with a finer resolution than the quanta of the three responses.

The subjective data can be collected from the patient at set times, or, alternatively, collected whenever the patient feels like providing subjective data. The subjective data can also be collected substantially contemporaneously with physiological data to provide greater insight into overall patient wellness. The subjective device 106 can be any device that accepts input from a patient or other concerned individual and/or provides information in a format that is recognizable to the patient. Device 106 typically includes a keypad, mouse, display, handheld device, interactive TV, cellular telephone or other radio frequency ("RF") communications device, cordless phone, corded phone, speaker, microphone, email message, or physical stimulus.

Figure 2:
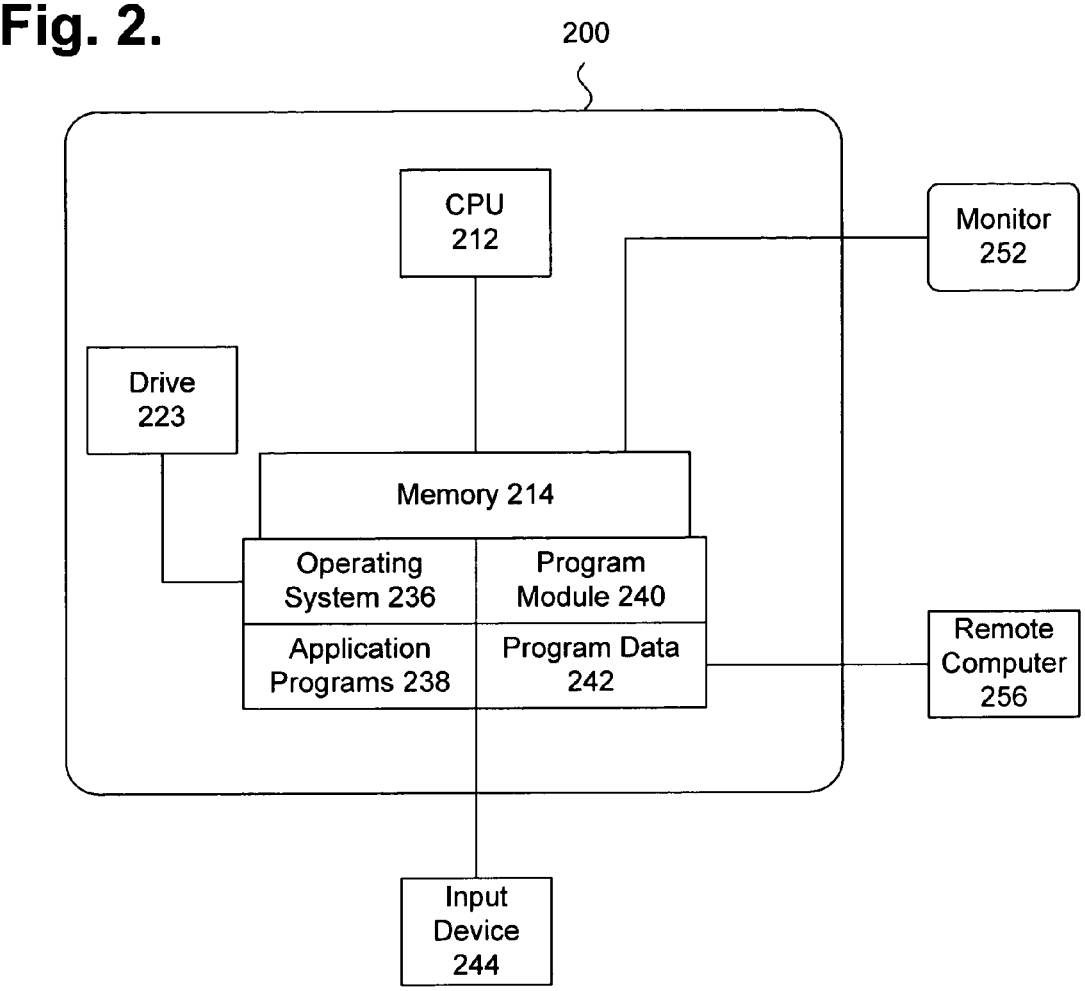
FIG. 2 illustrates an example computer system for use with the advanced patient management system.

In one example embodiment, the subjective device 106 includes or is part of a computer system 200, as illustrated in FIG. 2. The example computer system 200 includes a central processor unit 212 and a system memory 214. The computer system 200 further includes one or more drives 223 for reading data from and writing data to, as well as an input device 244, such as a keyboard or mouse, and a monitor 252 or other type of display device. A number of program modules may be stored on the drive 223, including an operating system 236, one or more application programs 238, other program modules 240, and program data 242. The computer system 200 can operate in a networked environment using logical connections to one or more remote computers or computer systems 256. Computer system 200 can also include hand-held computers such as a PDA computer.

The advanced patient management system 100 may also include one or more remote peripheral devices 109. The remote peripheral device 109 may include, for example and without limitation, cellular telephones, pagers, PDA devices, facsimiles, remote computers, printers, video and/or audio devices, etc. The remote peripheral device 109 can communicate using wired or wireless technologies and may be used by the patient or caregiver to communicate with the communication system 110 and/or the host 112. For example, the remote peripheral device 109 can be used by the caregiver to receive alerts from the host 112 based on data collected from the patient and to send instructions from the caregiver to either the patient or other clinical staff. In another example, the remote peripheral device 109 is used by the patient to receive periodic or real time updates and alerts regarding the patient's health and well-being.

Interrogator/Transceiver Unit

Figure 3:
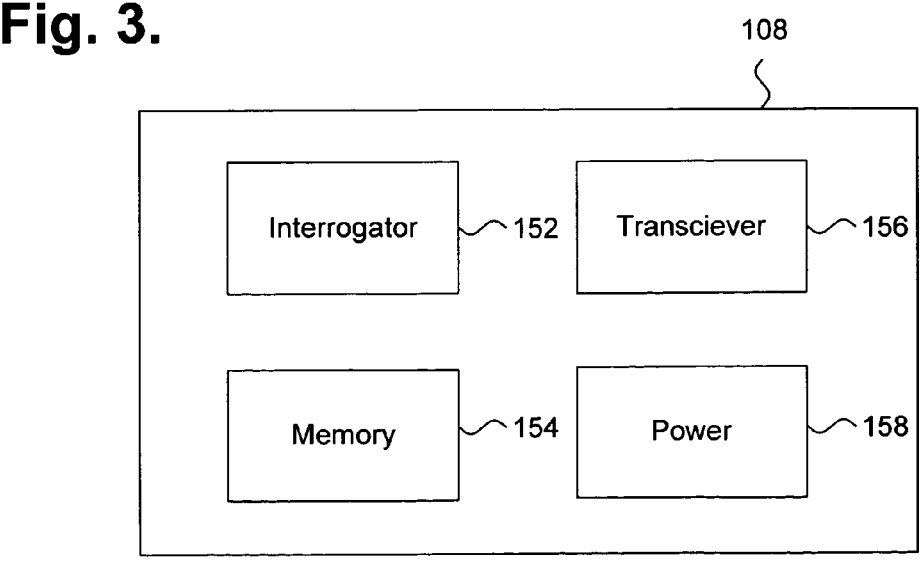
FIG. 3 illustrates an example interrogator/transceiver unit for use with the advanced patient management system.

Referring now to FIG. 3, the example advanced patient management system 100 includes one or more interrogator/transceiver units ("ITUs"), such as ITU 108. The ITU 108 includes an interrogator module 152 for sending and receiving data from a device, such as devices 102, 104, and 106, a memory module 154 for storing data, and a transceiver module 156 for sending and receiving data to and from other components of the APM system 100. The transceiver module may also operate as an interrogator of the devices 102, 104 and 106. The ITU 108 also includes a power module 158 that provides power.

The ITU 108 may perform one or more of the following functions: (1) data storage; (2) data analysis; (3) data forwarding; (4) patient interaction; (5) patient feedback; and (6) data communications. For example, the ITU 108 may facilitate communications between the devices 102, 104, and 106 and the communication system 110. The ITU 108 can, periodically or in real-time, interrogate and download into memory clinically relevant patient data from the devices 102, 104, and/or 106. This data includes, in the cardiac sensor context, for example, P and R-wave measurements, pacing, shocking events, lead impedances, pacing thresholds, battery voltage, capacitor charge times, ATR episodes with electrograms, tachycardia episodes with electrograms, histogram information, and any other clinical information necessary to ensure patient health and proper device function. The data is sent to the ITU 108 by the devices 102, 104, and 106 in real-time or periodically uploaded from buffers in the devices.

The ITU 108 may also allow patient interaction. For example, the ITU 108 may include a patient interface and allow the patient to input subjective data. In addition, the ITU 108 may provide feedback to the patient based on the data that has been analyzed or based on information communicated by the communication system 110.

In another embodiment, the ITU 108 includes a telemetry link from the devices to a network that forms the basis of a wireless LAN in the patient's home. The ITU 108 systematically uploads information from the devices 102, 104, and/or 106 while the patient is sleeping, for example. The uploaded data is transmitted through the communication system 110 or directly to the host 112. In addition, in one embodiment the ITU 108 functions in a hybrid form, utilizing wireless communication when available and defaulting to a local wireless portal or a wired connection when the wireless communication becomes unavailable.

Some devices, such as legacy implanted cardiac rhythm management ("CRM") devices, communicate via an internal telemetry transceiver that communicates with an external programmer. The communication range of such devices is typically 1 to 4 inches. ITU 108 may include a special short-range interrogator that communicates with a legacy device.

When the interrogator 152 uses radio frequency to communicate with the devices 102, 104, 106, the ITU 108 may be in the form of a small device that is placed in an inconspicuous place within the patient's residence. Alternatively, the ITU 108 may be implemented as part of a commonly-used appliance in the patient's residence. For example, the ITU may be integrated with an alarm clock that is positioned near the patient's bed. In another embodiment, the ITU may be implemented as part of the patient's personal computer system. Other embodiments are also possible.

In another embodiment, the ITU 108 may comprise a hand-held device such as a PDA, cellular telephone, or other similar device that is in wireless communication with the devices 102, 104, and 106. The hand-held device may upload the data to the communication system 110 wirelessly. Alternatively, the hand-held device may periodically be placed in a cradle or other similar device that is configured to transmit the data to the communication system 110.

In one embodiment, the ITU 108 can perform analysis on the data and provide immediate feedback, as well as perform a variety of self-diagnostic tests to verify that it is functioning properly and that communication with the communication system 110 has not be compromised. For example, the ITU 108 can perform a diagnostic loop-back test at a time set by the host 112, which involves sending a request through the communication system 110 to the host 112. The host 112 can then reply with a response back through the communication system 110 to the ITU 108. If a specific duration elapses before the ITU 108 receives the response or the ITU 108 receives an unexpected response, or if the host 112 does not receive the diagnostic test communication, the ITU 108 can provide indications that the system is not functioning properly and the host 112 can alert an operator that there may be compromised communications with that specific ITU 108. For example, if wireless communications between the ITU 108 and the communication system 110 have been interrupted, and the ITU 108 performs a self-diagnostic test that fails, the ITU 108 may alert the patient so that corrective action may be taken. The alert can take the form of a sound or a visual and/or audible annunciator to alert the patient that communication has been interrupted. In another embodiment, the ITU 108 can automatically fail-back to a wired system to communicate with the communication system 110 and perform the same communications compromise checks.

In other embodiments of the advanced patient management system 100, the ITU 108 function can be integrated into devices 102, 104, and 106, so that the devices can communicate directly with the communication system 110 and/or host 112. The devices 102, 104 and 106 can incorporate multi-mode wireless telecommunications such as cellular, BLUETOOTH, or IEEE 802.11 B to communicate with the communication system 110 directly or through a local wireless to a wired portal in the patients' home. For example, device 102 may include a miniature cellular phone capable of wirelessly uploading clinical data from the device on a periodic basis. This is particularly advantageous for devices that are mobile (e.g., an implanted device in a patient that is traveling).

To conserve the energy of the devices 102, 104, and 106, particularly when the devices (e.g., device 102) are configured to communicate directly with the communication system 110 without using an ITU 108, in one example embodiment the devices are configured to communicate during a given duty cycle. For example, the device 102 can be configured to communicate with the communication system 110 at given intervals, such as once a week. The device 102 can record data for the time period (e.g., a week) and transmit the data to the communication system 110 during the portion of the cycle that transmission is active and then conserve energy for the rest of the cycle. In another example, the device 102 conserves energy and only communicates with the communication system 110 when an "interesting" event, such as a heart arrhythmia, has occurred. In this manner, device 102 can communicate directly with the communication system 110 and/or host 112 without requiring an ITU 108, while conserving the energy of the device by communicating only during a given duty cycle.

The interrogation rate of the ITU 108 can be varied depending on disease state and other relevant factors. In addition, the devices 102, 104, and 106 can be configured to "wake up" frequently (e.g., once every couple minutes) to provide the ITU 108 an access window for the ITU 108 to provide commands to the devices 102, 104, and 106, as well as upload data from the devices.

If multiple devices, such as devices 102, 104, and 106, are provided for a given patient, each device may include its own means for communicating with the ITU 108 or communication system 110. Alternatively, a single telemetry system may be implemented as part of one of the devices, or separate from the devices, and each device 102, 104, and 106 can use this single telemetry system to communication with the ITU 108 or the communication system 110.

In yet another embodiment, the devices 102, 104, and 106 include wires or leads extending from devices 102, 104, and 106 to an area external of the patient to provide a direct physical connection. The external leads can be connected, for example, to the ITU 108 or a similar device to provide communications between the devices 102, 104, and 106 and the other components of the advanced patient management system 100.

The advanced patient management system 100 can also involve a hybrid use of the ITU 108. For example, the devices 102, 104, and 106 can intelligently communicate via short-range telemetry with the ITU when the patient is located within the patient's home and communicate directly with the communication system 110 or host 112 when the patient is traveling. This may be advantageous, for example, to conserve battery power when the devices are located near an ITU.

Communication System

Figure 4:
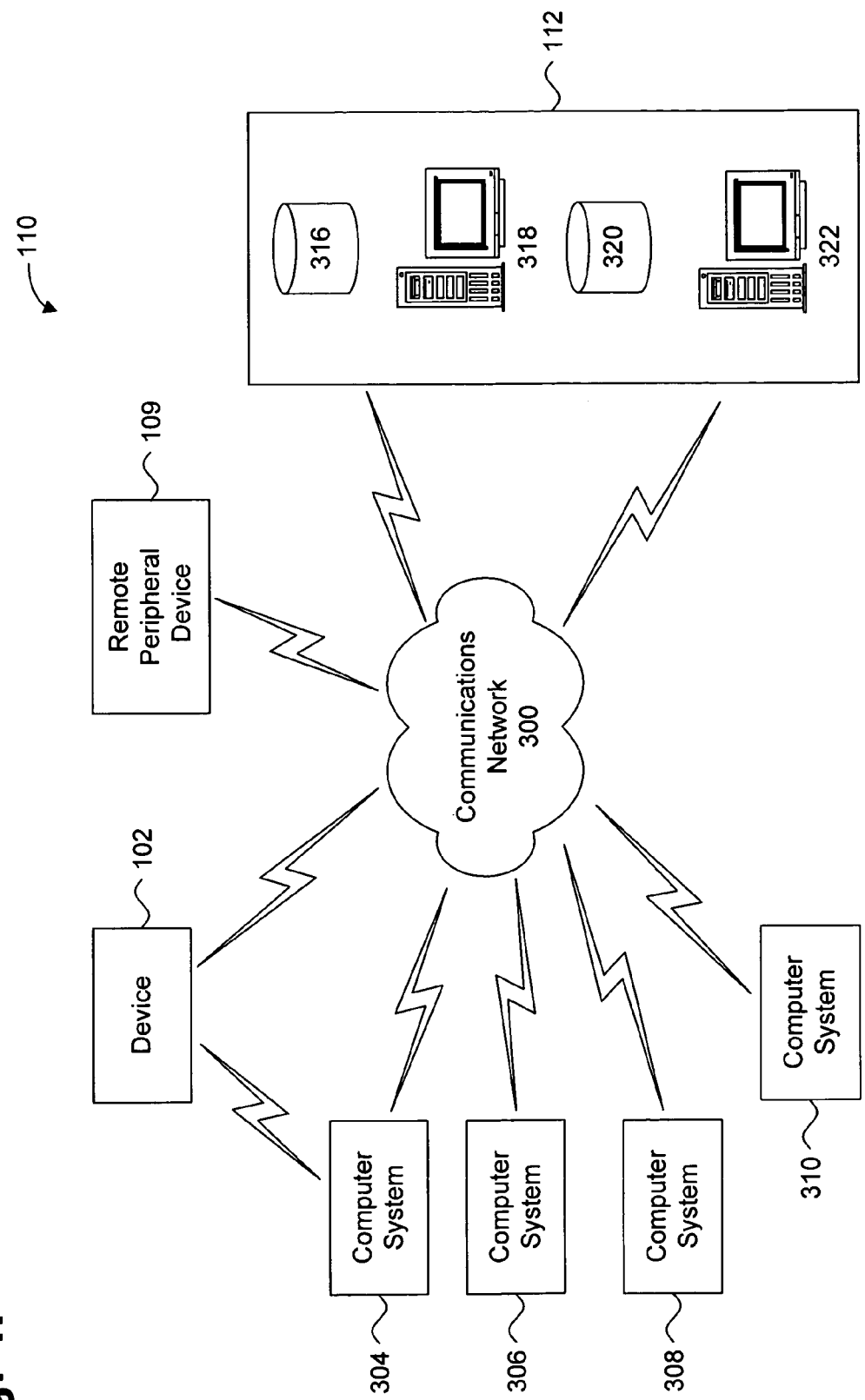
FIG. 4 illustrates an example communication system for use with the advanced patient management system.

Communication system 110 provides for communications between and among the various components of the advanced patient management system 100, such as the devices 102, 104, and 106, host 112, and remote peripheral device 109. FIG. 4 illustrates one embodiment for the communication system 110. The communication system 110 includes a plurality of computer systems 304, 306, 308, and 310, as well as device 102, host 112, and remote peripheral device 109, connected to one another by the communications network 300. The communications network 300 may be, for example, a local area network (LAN), wide area network (WAN), or the Internet. Communications among the various components, as described more fully below, may be implemented using wired or wireless technologies.

In the example embodiment illustrated, the host 112 includes server computers 318 and 322 that communicate with computers 304, 306, 308, and 310 using a variety of communications protocols, described more fully below. The server computers 318 and 322 store information in databases 316 and 320. This information may also be stored in a distributed manner across one or more additional servers.

A variety of communication methods and protocols may be used to facilitate communication between devices 102, 104, and 106, ITU 108, communication system 110, host 112, and remote peripheral device 109. For example, wired and wireless communications methods may be used. Wired communication methods may include, for example and without limitation, traditional copper-line communications such as DSL, broadband technologies such as ISDN and cable modems, and fiber optics, while wireless communications may include cellular, satellite, radio frequency (RF), Infrared, etc.

For any given communication method, a multitude of standard and/or proprietary communication protocols may be used. For example and without limitation, protocols such as radio frequency pulse coding, spread spectrum, direct sequence, time-hopping, frequency hopping, SMTP, FTP, and TCP/IP may be used. Other proprietary methods and protocols may also be used. Further, a combination of two or more of the communication methods and protocols may also be used.

The various communications between the components of the advanced patient management system 100 may be made secure using several different techniques. For example, encryption and/or tunneling techniques may be used to protect data transmissions. Alternatively, a priority data exchange format and interface that are kept confidential may also be used. Authentication can be implemented using, for example, digital signatures based on a known key structure (e.g., PGP or RSA). Other physical security and authentication measures may also be used, such as security cards and biometric security apparatuses (e.g., retina scans, iris scans, fingerprint scans, veinprint scans, voice, facial geometry recognition, etc.). Conventional security methods such as firewalls may be used to protect information residing on one or more of the storage media of the advanced patient management system 100. Encryption, authentication and verification techniques may also be used to detect and correct data transmission errors.

Communications among the various components of the advanced patient management system 100 may be enhanced using compression techniques to allow large amounts of data to be transmitted efficiently. For example, the devices 102, 104, and 106 or the ITU 108 may compress the recorded information prior to transmitting the information to the ITU 108 or directly to the communication system 110.

The communication methods and protocols described above can facilitate periodic and/or real-time delivery of data.

Host

The example host 112 includes a database module 114, an analysis module 116, and a delivery module 118 (see FIG. 1). Host 112 preferably includes enough processing power to analyze and process large amounts of data collected from each patient, as well as to process statistics and perform analysis for large populations. For example, the host 112 may include a mainframe computer or multi-processor workstation. The host 112 may also include one or more personal computer systems containing sufficient computing power and memory. The host 112 may include storage medium (e.g., hard disks, optical data storage devices, etc.) sufficient to store the massive amount of high-resolution data that is collected from the patients and analyzed.

The host 112 may also include identification and contact information (e.g., IP addresses, telephone numbers, or a product serial number) for the various devices communicating with it, such as ITU 108 and peripheral device 109. For example, each ITU 108 is assigned a hard-coded or static identifier (e.g., IP address, telephone number, etc.), which allows the host 112 to identify which patient's information the host 112 is receiving at a given instant. Alternatively, each device 102, 104, and 106 may be assigned a unique identification number, or a unique patient identification number may be transmitted with each transmission of patient data.

When a device is first activated, several methods may be used to associate data received by the advanced patient management system 100 with a given patient. For example, each device may include a unique identification number and a registration form that is filled out by the patient, caregiver, or field representative. The registration form can be used to collect the necessary information to associate collected data with the patient. Alternatively, the user can logon to a web site to allow for the registration information to be collected. In another embodiment, a barcode is included on each device that is scanned prior to or in conjunction deployment of the device to provide the information necessary to associate the recorded data with the given patient.

Referring again to FIG. 1, the example database module 114 includes a patient database 400, a population database 402, a medical database 404, and a general database 406, all of which are described further below.

The patient database 400 includes patient specific data, including data acquired by the devices 102, 104, and 106. The patient database 400 also includes a patient's medical records. The patient database 400 can include historical information regarding the devices 102, 104, and 106. For example, if device 102 is an implantable cardioverter defibrillator (ICD), the patient database 400 records the following device information: P and R measurements, pacing frequency, pacing thresholds, shocking events, recharge time, lead impedance, battery voltage/remaining life, ATR episode and EGMs, histogram information, and other device-specific information. The information-stored in the database 400 can be recorded at various times depending on the patient requirements or device requirements. For example, the database 400 is updated at periodic intervals that coincide with the patient downloading data from the device. Alternatively, data in the database 400 can be updated in real time. Typically, the sampling frequency depends on the health condition being monitored and the co-morbidities.

The population database 402 includes non-patient specific data, such as data relating to other patients and population trends. The population database 402 also records epidemic-class device statistics and patient statistics. The population database 402 also includes data relating to staffing by health care providers, environmental data, pharmaceuticals, etc.

The example medical database 404 includes clinical data relating to the treatment of diseases. For example, the medical database 404 includes historical trend data for multiple patients in the form of a record of progression of their disease(s) along with markers of key events.

The general database 406 includes non-medical data of interest to the patient. This can include information relating to news, finances, shopping, technology, entertainment, and/or sports. The general database 406 can be customized to provide general information of specific interest to the patient. For example, stock information can be presented along with the latest health information as detected from the devices 102, 104, and 106.

In another embodiment, information is also provided from an external source, such as external database 600. For example, the external database 600 includes external medical records maintained by a third party, such as drug prescription records maintained by a pharmacy, providing information regarding the type of drugs that have been prescribed for a patient.

The example analysis module 116 includes a patient analysis module 500, device analysis module 502, population analysis module 504, and learning module 506.

Patient analysis module 500 may utilize information collected by the advanced patient management system 100, as well as information for other relevant sources, to analyze data related to a patient and provide timely and predictive assessments of the patient's well-being. In performing this analysis, the patient device module 500 may utilize data collected from a variety of sources, include patient specific physiological and subjective data collected by the advanced patient management system 100, medical and historical records (e.g., lab test results, histories of illnesses, etc., drugs currently and previously administered, etc.), as well as information related to population trends provided from sources external to the advanced patient management system 100.

For example, in one embodiment, the patient analysis module 500 makes a predictive diagnosis of an oncoming event based on information stored in the database module 114. For example, the data continuously gathered from a device of a given patient at a heightened risk for a chronic disease event (such as de-compensations in heart failure) is analyzed. Based on this analysis, therapy, typically device-based or pharmaceutical, is then be applied to the patient either through the device or through clinician intervention.

In another example embodiment, the patient analysis module 500 provides a diagnosis of patient health status and predicted trend based on present and recent historical data collected from a device as interpreted by a system of expert knowledge derived from working practices within clinics. For example, the patient analysis module 500 performs probabilistic calculations using currently-collected information combined with regularly-collected historical information to predict patient health degradation.

In another example embodiment, the patient analysis module 500 may conduct pre-evaluation of the incoming data stream combined with patient historical information and information from patients with similar disease states. The pre-evaluation system is based on data derived from working clinical practices and the records of outcomes. The derived data is processed in a neural network, fuzzy logic system, or equivalent system to reflect the clinical practice. Further, the patient analysis module 500 may also provide means for periodic processing of present and historical data to yield a multidimensional health state indication along with disease trend prediction, next phase of disease progression co-morbidities, and inferences about what other possible diseases may be involved. The patient analysis module 500 may also integrate data collected from internal and external devices with subjective data to optimize management of overall patient health.

Device analysis module 502 analyzes data from the devices 102, 104, and 106 and ITU 108 to predict and determine device issues or failures. For example, if an implanted device 102 fails to communicate at an expected time, device analysis module 502 determines the source of the failure and takes action to restore the performance of the device 102. The device analysis module 502 may also perform additional deterministic and probabilistic calculations. For example, the device analysis module 502 gathers data related to charge levels within a given device, such as an ICD, and provides analysis and alerting functions based on this information if, for example, the charge level reaches a point at which replacement of the device and/or battery is necessary. Similarly, early degradation or imminent failure of implanted devices can be identified and proactively addressed, or at-risk devices can be closely monitored.

Population analysis module 504 uses the data collected in the database module 114 to manage the health of a population. For example, a clinic managing cardiac patients can access the advanced patient management system 100 and thereby obtain device-supplied advance information to predict and optimize resource allocation both as to immediate care and as a predictive metric for future need of practicing specialists. As another example, the spread of disease in remote populations can be localized and quarantined rapidly before further spread.

In one embodiment, population analysis module 504 trends the patient population therapy and management as recorded by the devices and directs health care resources to best satisfy the needs of the population. The resources can include people, facilities, supplies, and/or pharmaceuticals. In other embodiments, the population analysis module detects epidemics and other events that affect large population groups. The population analysis module 504 can issue alerts that can initiate a population quarantine, redirect resources to balance size of staffing with number of presenting population, and predict future need of qualified specialists.

The population analysis module 504 may utilize a variety of characteristics to identify like-situated patients, such as, for example, sex, age, genetic makeup, etc. The population analysis module 504 may develop large amounts of data related to a given population based on the information collected by the advanced patient management system 100. In addition, the population analysis module 504 may integrate information from a variety of other sources. For example, the population analysis module 504 may utilize data from public domain databases (e.g., the National Institute of Health), public and governmental and health agency databases, private insurance companies, medical societies (e.g., the American Heart Association), and genomic records (e.g., DNA sequences).

In one embodiment of the invention, the host 112 may be used as a "data clearinghouse," to gather and integrate data collected from the devices 102, 104, and 106, as well as data from sources outside the advanced patient management system 100. The integrated data can be shared with other interested entities, subject to privacy restrictions, thereby increasing the quality and integration of data available.

Learning module 506 analyzes the data provided from the various information sources, including the data collected by the advanced patient system 100 and external information sources. For example, the learning module 506 analyzes historical symptoms, diagnoses, and outcomes along with time development of the diseases and co-morbidities. The learning module 506 can be implemented via a neural network (or equivalent) system.

The learning module 506 can be partially trained (i.e., the learning module 506 may be implemented with a given set of preset values and then learn as the advanced patient management system functions) or untrained (i.e., the learning module 506 is initiated with no preset values and must learn from scratch as the advanced patient management system functions). In other alternative embodiments, the learning module 506 may continue to learn and adjust as the advanced patient management system functions (i.e., in real time), or the learning module 506 may remain at a given level of learning and only advanced to a higher level of understanding when manually allowed to do so.

In a neural network embodiment, new clinical information is presented to create new neural network coefficients that are distributed as a neural network knowledge upgrade. The learning module 506 can include a module for verifying the neural network conclusions for clinical accuracy and significance. The learning module can analyze a database of test cases, appropriate outcomes and relative occurrence of misidentification of the proper outcomes. In some embodiments, the learning module 506 can update the analysis module 116 when the analysis algorithms exceed a threshold level of acceptable misidentifications.

The example learning module 506 uses various algorithms and mathematical modeling such as, for example, trend and statistical analysis, data mining, pattern recognition, cluster analysis, neural networks and fuzzy logic. Learning module 506 may perform deterministic and probabilistic calculations. Deterministic calculations include algorithms for which a clear correlation is known between the data analyzed and a given outcome. For example, there may be a clear correlation between the energy left in a battery of an implantable device and the amount of time left before the battery must be replaced.

A probabilistic calculation involves the correlation between data and a given outcome that is less than 100 percent certain. Probabilistic determinations require an analysis of several possible outcomes and an assignment of probabilities for those outcomes (e.g., an increase in weight of a patient may, at a 25% probability, signal an impending de-compensation event and/or indicate that other tests are needed). The learning module 506 performs probabilistic calculations and selects a given response based on less than a 100% probability. Further, as the learning module 506 "learns" for previous determinations (e.g., through a neural network configuration), the learning module 506 becomes more proficient at assigning probabilities for a given data pattern, thereby being able to more confidently select a given response. As the amount of data that has been analyzed by the learning module 506 grows, the learning module 506 becomes more and more accurate at assigning probabilities based on data patterns. A bifurcated analysis may be performed for diseases exhibiting similar symptoms. As progressive quantities of data are collected and the understanding of a given disease state advances, disease analysis is refined where a former singular classification may split into two or more sub-classes.

In addition, patient-specific clinical information can be stored and tracked for hundreds of thousands of individual patients, enabling a first-level electronic clinical analysis of the patient's clinical status and an intelligent estimate of the patient's short-term clinical prognosis. The learning module 506 is capable of tracking and forecasting a patient's clinical status with increasing levels of sophistication by measuring a number of interacting co-morbidities, all of which may serve individually or collectively to degrade the patient's health. This enables learning module 506, as well as caregivers, to formulate a predictive medical response to oncoming acute events in the treatment of patients with chronic diseases such as heart failure, diabetes, pain, cancer, and asthma/COPD, as well as possibly head-off acute catastrophic conditions such as MI and stroke.

Delivery module 118 coordinates the delivery of feedback based on the analysis performed by the host 112. In response to the analysis module 116, delivery module 118 can manage the devices 102, 104, and 106, perform diagnostic data recovery, program the devices, and otherwise deliver information as needed. In some embodiments, the delivery module 118 can manage a web interface that can be accessed by patients or caregivers. The information gathered by an implanted device can be periodically transmitted to a web site that is securely accessible to the caregiver and/or patient in a timely manner. In other embodiments, a patient accesses detailed health information with diagnostic recommendations based upon analysis algorithms derived from leading health care institutions.

For example, the caregiver and/or patient can access the data and analysis performed on the data by accessing one or more general content providers. In one example, the patient's health information is accessed through a general portal such as My Yahoo provided by Yahoo! Inc. of Sunnyvale, Calif. A patient can access his or her My Yahoo homepage and receive information regarding current health and trends derived from the information gathered from the devices 102, 104, and 106, as well as other health information gathered from other sources. The patient may also access other information in addition to health information on the My Yahoo website, such as weather and stock market information. Other electronic delivery methods such as email, facsimile, etc. can also be used for alert distribution.

In an alternative embodiment, the data collected and integrated by the advanced patient system 100, as well as any analysis performed by the system 100, is delivered by delivery module 118 to a caregiver's hospital computer system for access by the caregiver. A standard or custom interface facilitates communication between the advanced patient management system 100 and a legacy hospital system used by the caregiver so that the caregiver can access all relevant information using a system familiar to the caregiver.

The advanced patient management system 100 can also be configured so that various components of the system (e.g., ITU 108, communication system 110, and/or host 112) provide reporting to various individuals (e.g., patient and/or caregiver). For example, different levels of reporting can be provided by (1) the ITU 108 and (2) the host 112. The ITU 108 may be configured to conduct rudimentary analysis of data gathered from devices 102, 104, and 106, and provide reporting should an acute situation be identified. For example, if the ITU 108 detects that a significant heart arrhythmia is imminent or currently taking place, the ITU 108 provides reporting to the patient in the form of an audible or visual alarm.

The host 112 can provide a more sophisticated reporting system. For example, the host 112 can provide exception-based reporting and alerts that categorize different reporting events based on importance. Some reporting events do not require caregiver intervention and therefore can be reported automatically. In other escalating situations, caregiver and/or emergency response personnel need to become involved. For example, based on the data collected by the advanced patient management system 100, the delivery module 118 can communicate directly with the devices 102, 104, and 106, contact a pharmacy to order a specific medication for the patient, and/or contact 911 emergency response. In an alternative embodiment, the delivery module 118 and/or the patient may also establish a voice communication link between the patient and a caregiver, if warranted.

In addition to forms of reporting including visual and/or audible information, the advanced patient management system 100 can also communicate with and reconfigure one or more of the devices 102, 104, and 106. For example, if device 102 is part of a cardiac rhythm management system, the host 112 can communicate with the device 102 and reconfigure the therapy provided by the cardiac rhythm management system based on the data collected from one or more of the devices 102, 104, and 106. In another embodiment, the delivery module 118 can provide to the ITU 108 recorded data, an ideal range for the data, a conclusion based on the recorded data, and a recommended course of action. This information can be displayed on the ITU 108 for the patient to review or made available on the peripheral device 109 for the patient and/or clinician to review.

One or more headings have been provided above to assist in describing the various embodiments disclosed herein. The use of headings, and the resulting division of the description by the headings, should not be construed as limiting in any way. The subject matter described under one heading can be combined with subject matter described under one or more of the other headings without limitation and as desired.

Repeater Communications

Figure 5:
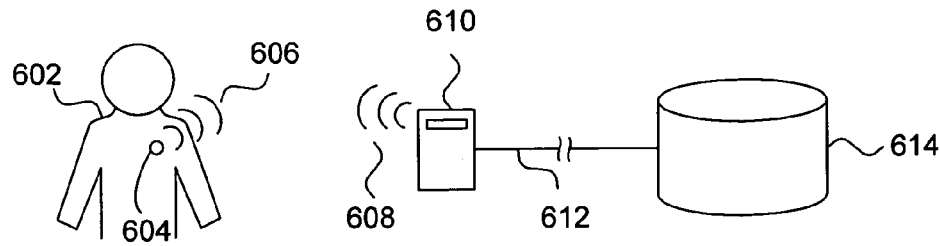
FIG. 5 illustrates communication between an implantable medical device, an external repeater device, and a repository.

FIG. 5 shows a patient 602 that has a medical device 604 coupled thereto. In this example, the medical device 604 is an implantable medical device such as a pacemaker. The medical device 604 communicates bi-directionally with a repeater device 610, such as an ITU 108 described above, by sending signals 606 to the repeater 610 and receiving signals 608 sent by the repeater 610. Signals 606, 608 can be achieved through inductive coupling, RF electromagnetic signaling, acoustic signaling, or other signaling methods known in the art. Furthermore, the signaling may occur wirelessly or through a wired connection, depending upon whether the device 604 is implanted or external to the patient's body 602.

Typically, an implanted medical device 604 will communicate using on-board telemetry as is known in the art. The on-board telemetry of the implanted medical device 604 performs a handshake with an external device such as the repeater device 610 to establish communications. The repeater device 610 interrogates the medical device 604 to retrieve data that the medical device 604 has been storing in on-board memory. For example, an implantable medical device 604 may store the number of times a particular cardiac episode has occurred since the last time the repeater device 610 downloaded the data.

The repeater device 610 captures the data and stores it in on-board memory, as discussed in greater detail below. Subsequently, the repeater device 610 transmits the data through a communication medium 612 to a data repository 614, such as an advanced patient management system maintaining a database of patient information as discussed above. The communication medium 612 and associated form of communication between the repeater device 610 and the repository 614 can take on various forms known in the art as discussed above in relation to the communication system 110 of FIGS. 1 and 4.

For example, a public switched telephone network (PSTN) may be used whereby the repeater device 610 accesses the telephone line of the patient's home and places a call to a repository telephone number to establish the connection entirely through the PSTN. As one alternative, the repeater device 610 may utilize a dial-up connection or an always-on connection to an Internet Service Provider (ISP) where the repository 614 is accessible through the Internet. Additionally, as discussed above, the repeater device 610 may incorporate wireless communication abilities enabling the repeater device 610 to transmit data wirelessly to the PSTN or wireless Internet through a cellular base station.

As mentioned above, the communication between the repeater device 610 and the medical device 604 may be bi-directional so that the repeater device 610 can also send data to the medical device 604. Furthermore, the communication between the repeater device 610 and the repository 614 may be bi-directional. This enables the repeater device 610 to forward data from the medical device 604 to the repository 614 and also forward data from the repository 614 to the medical device 604.

For instance, the repeater device 610 may forward data from the medical device 604 to the repository 614. After analysis of the data at the repository 614, it may be determined that reprogramming of the medical device 604 is necessary to compensate for a change in the patient's condition. The new programming may then be transferred from the repository 614 through the repeater device 610 to the medical device 604 where it can be implemented.

Figure 6:
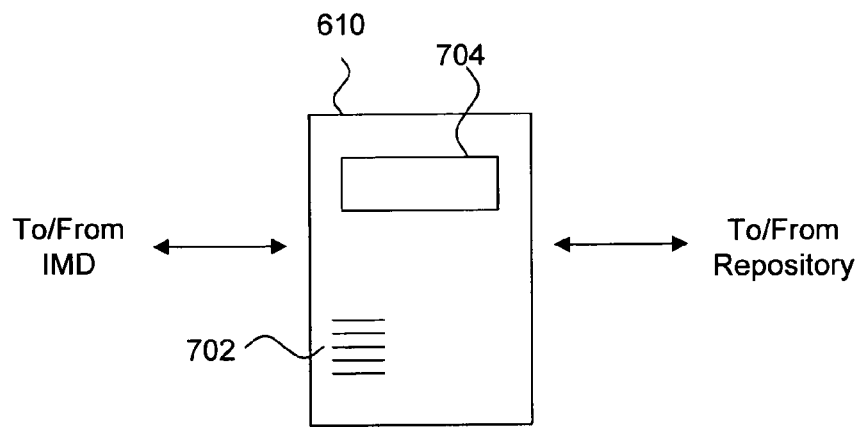
FIG. 6 illustrates exemplary external repeater device of FIG. 5 in more detail.

FIG. 6 is a view of an exemplary repeater device 610. The repeater device 610 may include audio and/or visual annunciation abilities to communicate progress and or alerts to the patient 602. For example, a liquid crystal display (LCD) 704 may be included to provide a visual cue to the patient about progress of upload from the medical device 604 and the progress of download to the repository 614. Furthermore, LCD 704 may be used to provide instructions for use of the medical device 604 and/or repeater device 610 as well as alerts. Similarly, an audio speaker 702 may provide audible cues including progress reports and warnings to the patient 602. Various other types of annunciation may be employed as well, including light emitting diodes (LEDs), etc.

In some embodiments, the repeater device 610 may include intelligence for analyzing the data being retrieved from the medical device 604. For example, the repeater device 610 may include programming that analyzes the data for episodes of cardiac activity that are precursors to a serious cardiac event. In this case, the repeater device 610 may annunciate to the patient 602 that a visit to a physician is necessary and immediately notify the repository 614 of the emergency situation. Likewise, the data from the medical device 604 may indicate that the medical device 604 itself has a problem, such as a broken cardiac lead. The repeater device 610 may be programmed to recognize this condition from the retrieved data and annunciate to the patient 602 that a visit to the physician is necessary.

Figure 7:
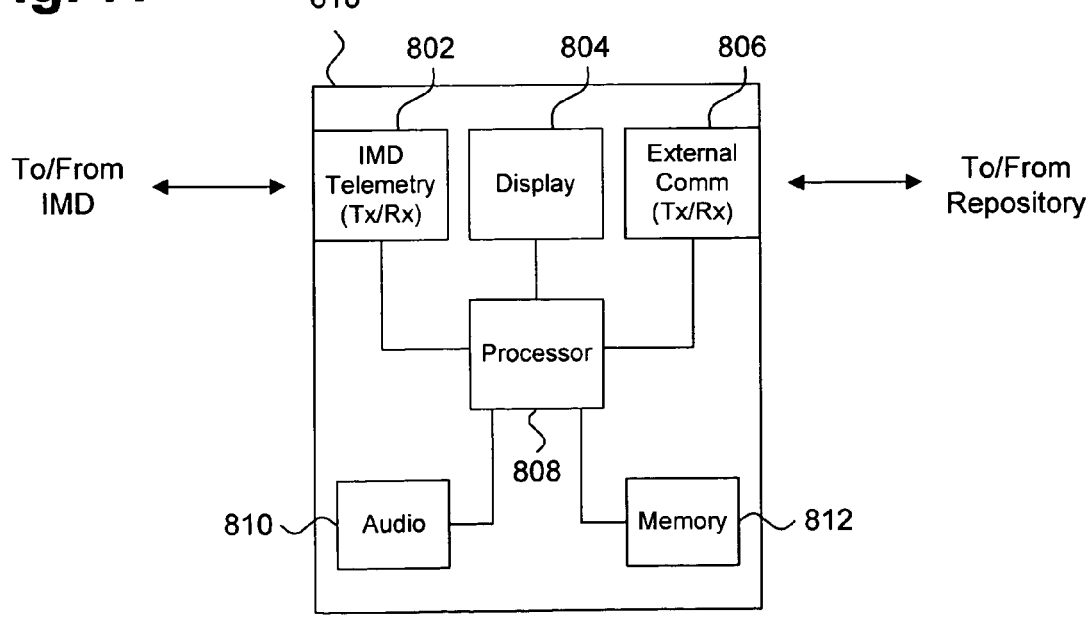
FIG. 7 illustrates components of the exemplary repeater device.

FIG. 7 is a view of the major components of the exemplary repeater device 610 of FIG. 5. This repeater device 610 contains telemetry 802 that enables communication with a medical device 604, such as an implantable medical device (IMD). As discussed above, such telemetry 802 may employ inductive coupling techniques to wirelessly transmit data to and from the repeater device 610. RF communications are a wireless alternative to inductive coupling and provide better range between the medical device 604 and the repeater device 610. Wired connections from the medical device 604 to telemetry 802 are another alternative for medical devices 604 worn externally.

The telemetry 802 demodulates or otherwise recovers data from the signal from the medical device 604 and provides the data to the processor 808. Alternatively, the telemetry 802 provides the received signal to the processor 808 which then demodulates or otherwise recovers the data from the signal. The processor 808 stores the data in memory 812, such as random access memory (RAM) where it can later be accessed. In certain embodiments, the processor 808 may perform data analysis to determine the urgency of the data.

Data analysis by the repeater 610 may include analyzing raw data recorded by the medical device 604 to detect physiological conditions and specific episodes. Data analysis may also include interpreting data generated by the medical device 604 that signals such conditions and episodes, such as where the medical device 604 analyzes raw data to determine the conditions and episodes prior to sending the data to the repeater 610. Data analysis of raw data to determine physiological condition and specific episodes is well known in the art, but examples include detecting cardiac arrhythmias, conduction disorders, pulse rate, episodes of tachycardia or bradycardia, and other physiological conditions.

The processor 808 provides the data from memory 812 to an external communications device 806, such as a telephone line interface (modem), a wireless digital or analog RF transceiver, and/or an always-on Internet connection (i.e., cable or DSL modem). The external communications device 806 interfaces with the communication medium 612 to transfer the data to the repository 614. Data transfer may occur through techniques well known in the art, including standard modulation techniques, circuit switched connections, and/or packet switched connections as is appropriate. The external communications device 806 is also configurable to receive data from the repository 614 through the communication medium 612.

The processor 808 controls annunciation devices including the display circuit 804 and audio circuit 810 to provide information to the user 602. The display circuit 804 controls the LCD display 704 to provide visual information such as instructions for use, problems with the repeater 610 or medical device 604, or emergency alerts. Likewise, the audio circuit 810 controls the speaker 702 to provide audible information.

Figure 9:
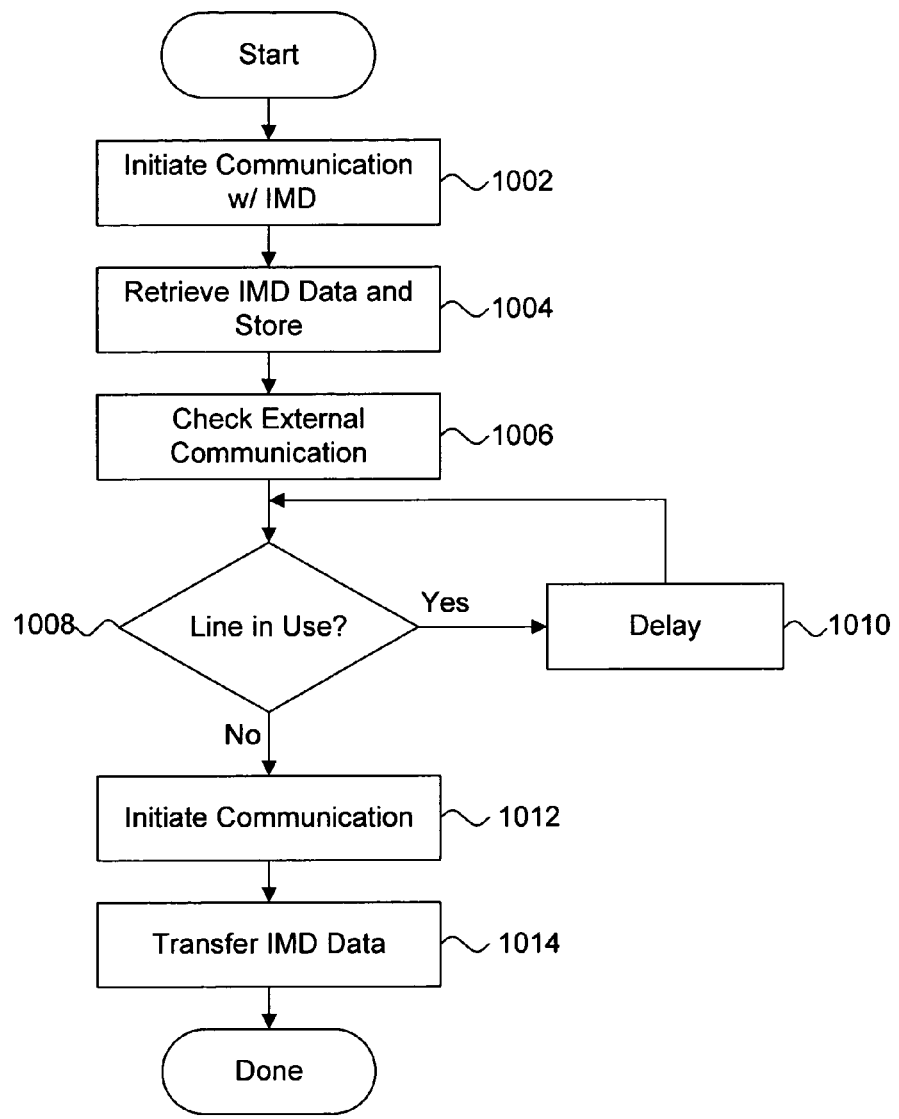
FIG. 9 illustrates an exemplary operational flow of communication between the implantable medical device, the external repeater device, and the repository where the condition of the communication medium is considered in relation to data transfer to the repository.
Figure 10:
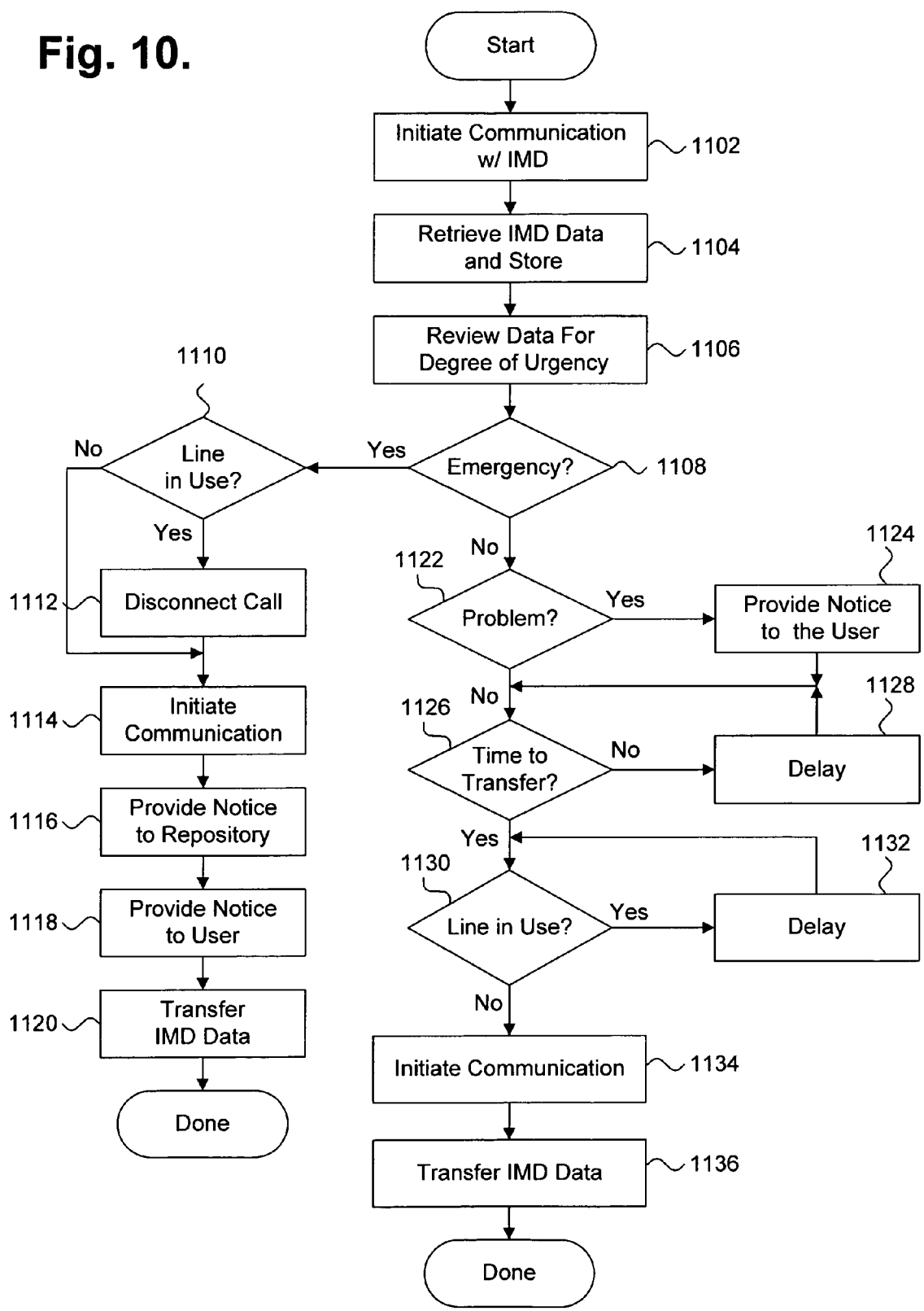
FIG. 10 illustrates an exemplary operational flow of communication between the implantable medical device, the external repeater device, and the repository where both the degree of urgency of the data and the condition of the communication medium are considered in relation to data transfer to the repository.

Logical operations of the processor 808 and its interaction with the various components shown in FIG. 7 are shown for several different embodiments in FIGS. 9-11. These logical operations of the various embodiments of the present invention are implemented (1) as a sequence of computer implemented acts or program modules and/or (2) as interconnected machine logic circuits or circuit modules. The implementation is a matter of choice dependent on the performance requirements of the repeater 610. Accordingly, the logical operations making up embodiments of the present invention described herein are referred to variously as operations, structural devices, acts, or modules. It will be recognized by one skilled in the art that these operations, structural devices, acts and modules may be implemented in software, in firmware, in special purpose digital logic, and any combination thereof without deviating from the spirit and scope of the present invention as recited within the claims attached hereto.

Figure 8:
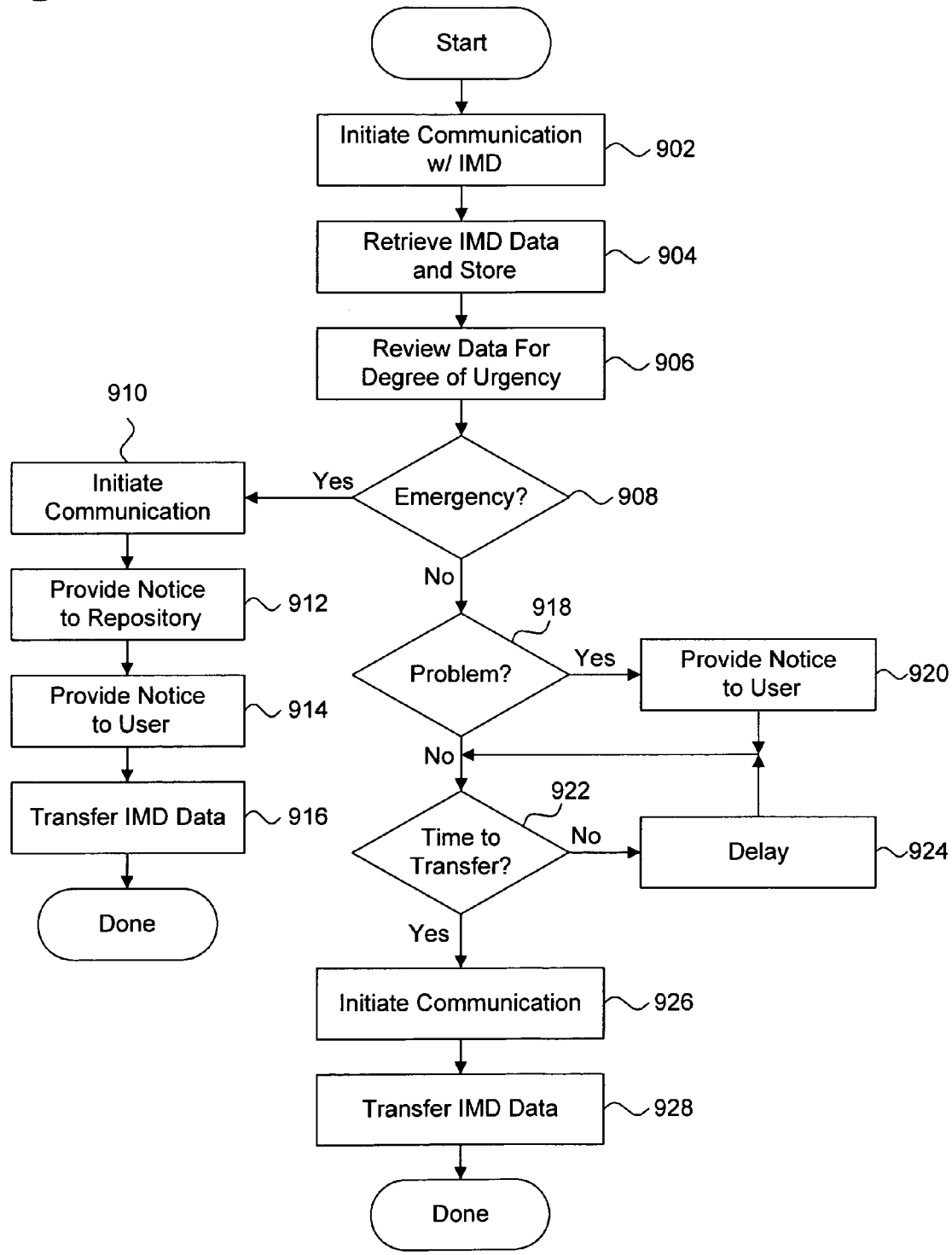
FIG. 8 illustrates an exemplary operational flow of communication between the implantable medical device, the external repeater device, and the repository where the degree of urgency of the data is determined and considered in relation to data transfer to the repository.

FIG. 8 shows exemplary logical operations where the repeater 610 considers the urgency of the data when coordinating the transfer of data to the repository 614. The operations begin with the processor 808 initiating communication with the medical device 604 through the telemetry 802 at communication operation 902. At data operation 904, the processor 808 retrieves the data through the telemetry 802 and stores the data in memory 812. At analysis operation 906, the processor 808 reviews the data to determine the degree of urgency. As discussed above, the processor 808 may review the data to determine whether the medical device 604 has found a specific condition or episode, or the processor 808 may employ its own analysis logic on the raw data recorded by the medical device 604 to find a specific condition or episode. In addition to or as an alternative to determining the degree of urgency based on analysis of the data, the processor may detect the degree of urgency by receiving input provided by a user. For example, the patient may press a button of the repeater that provides a signal to the processor 808 that the patient knows the data should be treated as urgent such as if a particular episode is occurring that the patient is aware of.

At query operation 908, the processor 808 detects from the analysis or otherwise whether the degree of urgency of the data indicates an emergency situation, such as where the data analysis shows that the user 602 needs immediate medical attention due to an imminent cardiac arrest or if the patient has indicated that the data is urgent. When the degree of urgency indicates an emergency situation, the repeater 610 proceeds to immediately initiate communication at communication operation 910. A notice of the emergency situation is transferred to the repository 614 at notice operation 912 to trigger an alarm so that repository personnel may take emergency action including dispatching paramedics to the user's location.

The repeater 610 also warns the user 602 of the emergency through visual and/or audible warnings at notice operation 914. The data stored in memory 812, including at least the data signaling the emergency situation, may then be transferred to the repository 614 at transfer operation 916. The repository personnel may then review the data to further assess the situation and assist paramedics.

If query operation 908 detects that there is no emergency, then query operation 918 tests whether the analyzed data indicates a problem. A problem may be detected from the data where the medical device 604 reports a malfunction, such as a broken cardiac lead, or reports other information that indicates the patient 602 should seek medical attention by some future point in time, although not immediately. If such a problem is detected, then the repeater 610 provides audible and/or visual notice of the problem to the user 602 at notice operation 920.

Once notice of the problem has been given to the user 602, or if query operation 918 detects no problem, then operational flow transitions to query operation 922 which detects whether it is an appropriate time to transfer data to the repository 614. For example, the repeater 610 may be configured so that transfers occur over a telephone line during low-activity periods such as 3 a.m. Other factors may be considered as well in addition to or as an alternative to the time of day. If query operation 922 detects that the proper time has arrived, then the processor 808 initiates communication with the repository 614 at communication operation 926. Data is then transferred to the repository 614 at transfer operation 928. If the proper time for transfer has not arrived, then the processor 808 waits out a delay 924, and then query operation 922 again detects whether the proper time has arrived.

FIG. 9 shows the logical operations where the repeater 610 considers the condition of the communication medium when coordinating transfer of data to the repository 614. The logical operations begin at communication operation 1002 where the repeater 610 initiates communication with the medical device 604. The repeater 610 retrieves the data from the medical device 604 and stores it in memory 812 at data operation 1004.

After the data has been obtained from the medical device 604, the repeater 610 checks the condition of the external communication medium 614 through interface 806 at test operation 1006. In this example, checking the condition of the communication medium 614 involves determining whether the telephone line is already in use. Other communication medium conditions may be determined as well. For example, if a wireless connection is being used to communicate with the repository 614, the strength of the wireless signal may be referenced to determine whether the signal is strong enough to communicate. As another example, if the Internet is being used to transfer data to the repository 614, the available bandwidth through the Internet connection may be determined to decide whether the data should be transferred.

The processor 808 may be configured so that test operation 1006 occurs as soon as the data has been retrieved or occurs at a later point in time, such as at a low-activity part of the day. After test operation 1006 has been performed, query operation 1008 detects whether the condition of the communication medium 614 is satisfactory. In this example, query operation 1008 detects whether the telephone line is in use. If so, the processor 808 stalls data transfer for a delay period 1010, and operational flow returns to test operation 1006 to again check the condition of the communication medium.

Once query operation 1008 detects that the telephone line is not in use, then communication operation 1012 initiates communication through the interface 806 with the repository 614. Once communication has been established, then data is transferred between the repeater device 610 and the repository 614 at transfer operation 1014.

FIG. 10 shows an example of logical operations of the repeater device 610 where both the urgency of the data and the condition of the communication medium are considered when coordinating data transfer to the repository 614. The operations begin with the processor 808 initiating communication with the medical device 604 through the telemetry 802 at communication operation 112. At data operation 1104, the processor 808 retrieves the data through the telemetry 802 and stores the data in memory 812. At analysis operation 1106, the processor 808 reviews the data to determine the degree of urgency.

At query operation 1108, the processor 808 detects from the analysis whether the degree of urgency of the data indicates an emergency situation, such as where the data analysis shows that the user 602 needs immediate medical attention due to an imminent cardiac arrest. When the degree of urgency indicates an emergency situation, the repeater 610 proceeds to immediately detect whether the telephone line is in use at query operation 1110. If so, then the telephone line interface 806 short circuits the telephone line to disconnect the current telephone call that is occupying the telephone line.

Once the telephone line has been freed or once query operation 1110 detects that the telephone line is not in use, the processor 808 initiates communication at communication-operation 1114. A notice of the emergency situation is transferred to the repository 614 at notice operation 1116 to trigger an alarm so that repository personnel may take emergency action including dispatching paramedics to the user's location.

The repeater 610 also warns the user 602 of the emergency through visual and/or audible warnings at notice operation 1118. The data stored in memory 812, including at least the data signaling the emergency situation, may then be transferred to the repository 614 at transfer operation 1120. The repository personnel may then review the data to further assess the situation and assist paramedics.

If query operation 1108 detects that there is no emergency, then query operation 1122 tests whether the analyzed data indicates a problem. As discussed above, a problem may be detected from the data where the medical device 604 reports a malfunction, such as a broken cardiac lead, or reports other information that indicates the patient 602 should seek medical attention by some future point in time, although not immediately. If such a problem is detected, then the repeater 610 provides audible and/or visual notice of the problem to the user 602 at notice operation 1124.

Once notice of the problem has been given to the user 602, or if query operation 1122 detects no problem, then operational flow transitions to query operation 1126 which detects whether it is an appropriate time to transfer data to the repository 614, such as during a low-activity period. If query operation 1126 detects that the proper time for transfer has not arrived, then the processor 808 waits out a delay 1128, and then query operation 1126 again detects whether the proper time has arrived.

If query operation 1126 detects that the proper time has arrived, then query operation 1130 detects whether the telephone line is in use. If so, then the processor 808 stalls for a delay period 1132 and then again checks the telephone line at query operation 1130. If the telephone line is not in use, then the processor 808 initiates communication with the repository 614 at communication operation 1134. Data is then transferred to the repository 614 at transfer operation 1136.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

What is claimed is:

1. A repeater for relaying data to a repository from a medical device coupled to a patient, comprising:
   a receiver configured to communicate with the medical device to obtain the data;
   a memory to maintain the data once it has been received;
   a transmission device configured to send the data over a wireless radio frequency connection to a data repository; and
   a processing device, comprising:
      a signal strength-based transceiver configured to detect a signal strength that is available through the wireless radio frequency connection and trigger the transmission device to send the data when the signal strength is adequate for transmission; and
      a patient urgency-based transceiver configured to detect a degree of urgency by analyzing the data to detect health conditions of the patient and trigger the transmission device to send the data at a time based on the degree of urgency.

2. A stored patient data set for use in remote patient care, comprising:
   information to identify a patient enrolled in automated patient care and comprising at least one of treatment profile information and medical history; and medical device data comprising a set of collected device data regularly recorded by a medical device and provided to a repository conditioned upon detecting an adequacy of a wireless radio frequency connection for transmission.

3. A stored patient data set according to claim 2, further comprising:
analysis data comprising a predictive assessment of patient well-being determined from the medical device data.

4. A stored patient data set according to claim 2, further comprising:
instructions comprising reprogramming data to be implemented by the medical device in response to a change in a health condition of the patient determined from the medical device data.

5. A stored patient data set according to claim 2, wherein the collected device data set is selected from the group comprising physiological, subjective, and environmental data.

6. A stored patient data set according to claim 2, wherein the patient identifying information and the medical device data are organized as a structured record.

7. A stored patient data set according to claim 6, wherein the structured record is maintained in a database.

8. A medical device providing a patient data set for use in automated patient care, comprising:
one or more sensors to monitor data of a patient enrolled in automated patient care as telemetered signals;
a memory to store the telemetered signals for a short term; and
an interface providing external access to the stored telemetered signals, wherein the stored telemetered signals are periodically retrieved and provided to a repository conditioned upon detecting an adequacy of a wireless radio frequency connection for transmission.

9. A medical device according to claim 8, further comprising:
a processor operating on instructions comprising reprogramming data to be implemented by the medical device in response to a change in a health condition of the patient determined from the medical device data.

10. A medical device according to claim 8, wherein the monitored data is selected from the group comprising physiological, subjective, and environmental data.

11. A medical device according to claim 8, wherein the medical device comprises at least one of an internal medical device and an external medical device.

12. An analysis system for providing a patient data set for use in automated patient care, comprising:
a database storing a plurality of sets of collected device data regularly recorded by a medical device for a patient enrolled in automated patient care; and
a processor receiving the collected device data sets from a repeater conditioned upon the repeater detecting an adequacy of a wireless radio frequency connection for transmission.

13. An analysis system according to claim 12, further comprising:
an analyzer to determine a predictive assessment of patient well-being from the medical device data and to store the predictive assessment in the database.

14. An analysis system according to claim 12, further comprising:
a programmer to determine a change in a health condition of the patient determined from the medical device data and to form instructions comprising reprogramming data to be implemented by the medical device in response to the change.

15. A structured record storing a patient data set for use in automated patient care, comprising:
structured data for a patient enrolled in automated patient care, comprising at least one of:
device data directly recorded by a medical device; and
device data derived from the directly recorded device data,
wherein the structured data is received from a repeater conditioned upon the repeater detecting an adequacy of a wireless radio frequency connection for transmission.

16. A structured record according to claim 15, further comprising at least one of:
analysis data comprising a predictive assessment of patient well-being determined from the medical device data; and
instructions comprising reprogramming data to be implemented by the medical device in response to a change in a health condition of the patient determined from the medical device data.

17. A structured record according to claim 15, wherein the monitored data is selected from the group comprising physiological, subjective, and environmental data.

18. A process for storing a patient data set for use in automated patient care, comprising:
storing a plurality of sets of collected device data regularly recorded by a medical device for a patient enrolled in automated patient care; and
receiving the collected device data Sets from a repeater conditioned upon the repeater detecting an adequacy of a wireless radio frequency connection for transmission.

19. A process according to claim 18, further comprising:
determining a predictive assessment of patient well-being from the medical device data and to store the predictive assessment in the database.

20. A process according to claim 18, further comprising:
determining a change in a health condition of the patient from the medical device data; and
forming instructions comprising reprogramming data to be implemented by the medical device in response to the change.

21. A computer-readable storage medium holding code for performing the process according to claim 18.

22. A stored patient data set for use in remote patient care, comprising:
information to identify a patient enrolled in automated patient care and comprising at least one of treatment profile information and medical history; and
medical device data comprising a set of collected device data regularly recorded by a medical device and provided to a repository at a time based on a degree of urgency determined from an analysis of a health condition of the patient.

23. A stored patient data set according to claim 22, further comprising:
analysis data comprising a predictive assessment of patient well-being determined from the medical device data.

24. A stored patient data set according to claim 22, further comprising:
instructions comprising reprogramming data to be implemented by the medical device in response to a change in a condition of the patient determined from the medical device data.

25. A stored patient data set according to claim 22, wherein the collected device data set is selected from the group comprising physiological, subjective, and environmental data.

26. A stored patient data set according to claim 22, wherein the patient identifying information and the medical device data are organized as a structured record.

27. A stored patient data set according to claim 26, wherein the structured record is maintained in a database.

28. A medical device providing a patient data set for use in automated patient care, comprising:
one or more sensors to monitor data of a patient enrolled in automated patient care as telemetered signals;
a memory to store the telemetered signals for a short term; and
an interface providing external access to the stored telemetered signals, wherein the stored telemetered signals are periodically retrieved and provided to a repository at a time based on a degree of urgency determined from an analysis of a health condition of the patient.

29. A medical device according to claim 28, further comprising:
a processor operating on instructions comprising reprogramming data to be implemented by the medical device in response to a change in a condition of the patient determined from the medical device data.

30. A medical device according to claim 28, wherein the monitored data is selected from the group comprising physiological, subjective, and environmental data.

31. A medical device according to claim 28, wherein the medical device comprises at least one of an internal medical device and an external medical device.

32. An analysis system for providing a patient data set for use in automated patient care, comprising:
a database storing a plurality of sets of collected device data regularly recorded by a medical device for a patient enrolled in automated patient care; and
a processor receiving the collected device data sets from a repeater at a time based on a degree of urgency determined from an analysis of a health condition of the patient.

33. An analysis system according to claim 32, further comprising:
an analyzer to determine a predictive assessment of patient well-being from the medical device data and to store the predictive assessment in the database.

34. An analysis system according to claim 32, further comprising:
a programmer to determine a change in a condition of the patient determined from the medical device data and to form instructions comprising reprogramming data to be implemented by the medical device in response to the change.

35. A structured record storing a patient data set for use in automated patient care, comprising:
structured data for a patient enrolled in automated patient care, comprising at least one of:
device data directly recorded by a medical device; and
device data derived from the directly recorded device data,
wherein the structured data is received from a repeater at a time based on a degree of urgency determined from an analysis of a health condition of the patient.

36. A structured record according to claim 35, further comprising at least one of:
analysis data comprising a predictive assessment of patient well-being determined from the medical device data; and
instructions comprising reprogramming data to be implemented by the medical device in response to a change in a condition of the patient determined from the medical device data.

37. A structured record according to claim 35, wherein the monitored data is selected from the group comprising physiological, subjective, and environmental data.

38. A process for storing a patient data set for use in automated patient care, comprising:
storing a plurality of sets of collected device data regularly recorded by a medical device for a patient enrolled in automated patient care; and
receiving the collected device data sets from a repeater at a time based on a degree of urgency determined from an analysis of a health condition of the patient.

39. A process according to claim 38, further comprising:
determining a predictive assessment of patient well-being from the medical device data and to store the predictive assessment in the database.

40. A process according to claim 38, further comprising:
determining a change in a condition of the patient from the medical device data; and
forming instructions comprising reprogramming data to be implemented by the medical device in response to the change.

41. A computer-readable storage medium holding code for performing the process according to claim 38.

* * * * *